(12) United States Patent
Ross

(10) Patent No.: US 9,539,458 B1
(45) Date of Patent: Jan. 10, 2017

(54) MULTI-POSITIONING EXERCISE MACHINE WITH DYNAMIC RESISTANCE

(71) Applicant: Michael Peter Ross, Carlsbad, CA (US)

(72) Inventor: Michael Peter Ross, Carlsbad, CA (US)

( * ) Notice: Subject to any disclaimer, the term of this patent is extended or adjusted under 35 U.S.C. 154(b) by 0 days.

(21) Appl. No.: 15/070,441

(22) Filed: Mar. 15, 2016

(51) Int. Cl.
| | | |
|---|---|---|
| *A63B 21/005* | (2006.01) | |
| *A63B 24/00* | (2006.01) | |
| *A63B 15/02* | (2006.01) | |
| *A63B 71/00* | (2006.01) | |
| *A63B 21/00* | (2006.01) | |
| *A63B 21/22* | (2006.01) | |
| *A63B 23/12* | (2006.01) | |

(52) U.S. Cl.
CPC ......... *A63B 21/0058* (2013.01); *A63B 21/154* (2013.01); *A63B 21/22* (2013.01); *A63B 21/4035* (2015.10); *A63B 21/4045* (2015.10); *A63B 23/12* (2013.01); *A63B 24/0062* (2013.01); *A63B 24/0087* (2013.01); *A63B 2225/50* (2013.01)

(58) Field of Classification Search
CPC ............ A63B 21/4045; A63B 21/4029; A63B 21/0058; A63B 21/0059; A63B 21/15; A63B 21/151; A63B 21/152; A63B 21/153; A63B 21/154; A63B 21/155; A63B 21/156; A63B 24/0087; A63B 23/12; A63B 24/0062; A63B 21/4035; A63B 21/22; A63B 2225/50
See application file for complete search history.

(56) References Cited

U.S. PATENT DOCUMENTS

| | | | | |
|---|---|---|---|---|
| 4,625,962 A | * | 12/1986 | Street | A63B 21/015 482/116 |
| 4,826,157 A | * | 5/1989 | Fitzpatrick | A63B 21/078 482/103 |
| 4,998,721 A | * | 3/1991 | Anders | A63B 21/078 482/104 |
| 5,048,826 A | * | 9/1991 | Ryan | A63B 21/00181 482/104 |
| 5,407,403 A | * | 4/1995 | Coleman | A63B 21/078 482/104 |
| 6,280,361 B1 | * | 8/2001 | Harvey | A63B 21/025 482/101 |
| 6,387,020 B1 | * | 5/2002 | Simonson | A63B 21/0628 482/102 |
| 6,599,223 B2 | * | 7/2003 | Wang | A63B 21/005 482/138 |

(Continued)

*Primary Examiner* — Joshua Lee

(57) ABSTRACT

An exercise machine which allows a user to perform a variety of exercises using dynamic resistance. The exercise machine includes a platform base, a housing tower, an upper-left exercise module, an upper-right exercise module, and a control console. The upper-left exercise module and the upper-right exercise module each comprise a primary torque motor, a primary cable, a pulley system, a structural arm, and a primary handle. The housing tower is connected onto the platform base. The upper-left exercise module and the upper-right exercise module are integrated into the housing tower and provide a means for applying a resistance force onto the extremities of the user. The primary cable tensionably engages the pulley system and connects the primary handle to the primary torque motor. The primary handle rests within and against the structural arm, attached to the housing tower. The control console allows for external device compatibility.

10 Claims, 13 Drawing Sheets

(56) References Cited

U.S. PATENT DOCUMENTS

| | | | |
|---|---|---|---|
| 6,712,740 B2 * | 3/2004 | Simonson | A63B 21/154 482/102 |
| 6,790,163 B1 * | 9/2004 | Van De Laarschot | A63B 21/0056 434/254 |
| 8,444,537 B1 * | 5/2013 | Santoro | A63B 21/078 482/104 |
| 8,517,899 B2 * | 8/2013 | Zhou | A63B 69/182 482/138 |
| 8,647,239 B1 * | 2/2014 | Sokolovas | A63B 69/10 482/55 |
| 9,403,047 B2 * | 8/2016 | Olson | A63B 21/00192 |
| 2002/0094918 A1 * | 7/2002 | Gerschefske | A63B 21/1672 482/92 |
| 2003/0045406 A1 * | 3/2003 | Stone | A63B 21/154 482/100 |
| 2005/0233871 A1 * | 10/2005 | Anders | A63B 21/0724 482/93 |
| 2006/0035755 A1 * | 2/2006 | Dalebout | A63B 21/00072 482/52 |
| 2007/0287601 A1 * | 12/2007 | Burck | A63B 21/153 482/54 |
| 2008/0051256 A1 * | 2/2008 | Ashby | A63B 21/00072 482/5 |
| 2010/0144496 A1 * | 6/2010 | Schmidt | A63B 21/012 482/70 |
| 2013/0303334 A1 * | 11/2013 | Adhami | A63B 21/025 482/4 |
| 2013/0310230 A1 * | 11/2013 | Norris | A63B 21/018 482/115 |
| 2014/0162854 A1 * | 6/2014 | Watterson | A63B 21/00196 482/138 |
| 2014/0274600 A1 * | 9/2014 | Dalebout | A63B 21/225 482/115 |
| 2015/0182780 A1 * | 7/2015 | Olson | A63B 21/156 482/139 |
| 2015/0352396 A1 * | 12/2015 | Dalebout | A63B 22/02 482/54 |

\* cited by examiner

DETAIL A

MULTI-POSITIONING EXERCISE MACHINE WITH DYNAMIC RESISTANCE

FIELD OF THE INVENTION

The present invention relates generally to exercise apparatus. More specifically, the present invention is a multi-positioning exercise machine which utilizes a multitude of torque motors to provide a user with dynamic programmable resistance.

BACKGROUND OF THE INVENTION

Exercise has many health benefits for an individual. As a result, many individuals make an attempt to maintain good physical fitness. A major component of maintaining good physical fitness is promoting muscular strength and endurance and/or stamina. Many exercise options are available for promoting muscular strength and endurance and/or stamina. Forms of static and anaerobic exercise include activities such as weightlifting and are used to build muscular strength. Forms of dynamic and aerobic exercise include activities such as running or jogging and are used to increase muscular endurance and stamina. Muscular endurance may also be increased by performing more repetitions of a movement using a smaller amount of weight. A wide variety of exercise machines are available for performing many of these exercises. In spite of the plethora of machines and equipment available, individuals have a difficult time determining how effectively they are using these different machines and equipment and cannot evaluate their overall muscular health.

It is therefore an object of the present invention to provide an exercise machine that not only allows the user to perform a variety of different exercises but also tracks and measures the muscular health of the user based on his or her performance. Individuals may use the present invention to assist in building joint and muscle flexibility, range of motion of individual limbs, sense of balance and stability, and to perform rehabilitation functions. In addition, the present invention is highly compatible with various external computing devices and applications which may act as a personal trainer to the user in order to customize a workout routine that is based on the user's fitness level. Furthermore, the present invention may be used to enhance a variety of sport activities including, but not limited to, tennis, gold, baseball, rowing, and skiing.

DETAIL DESCRIPTIONS OF THE INVENTION

All illustrations of the drawings are for the purpose of describing selected versions of the present invention and are not intended to limit the scope of the present invention.

The present invention generally relates to exercise machines. More specifically, the present invention is a multi-positioning exercise machine that uses an electric motor, a torque motor to be more specific, in order to provide a user with dynamic resistance. Exercise is achieved by pulling on one or two cable handles under a resistance load; each cable handle is tethered to an electric motor that applies the resistance load. The present invention includes a modular seat and up to four of said cable handles, thus allowing for the user to perform a variety of different exercises. In addition, the present invention also measures and tracks the physical performance of the user in order to generate reflective workout statistics. The user is able to connect with the present invention through a wireless connection or a direct wired connection in order to view the workout statistics, control and set resistance settings, and view/receive continuous updates. The user may perform a variety of different exercises at his or her discretion with the present invention. The user is also provided with the option to perform a customized exercise routine; a routine tailored for the user based on the physical fitness of the user, physical goals provided by the user, and other similar descriptive inputs received from the user. Additionally, the customized exercise routine may be remotely provided to the user from a personal trainer.

Figure 1:
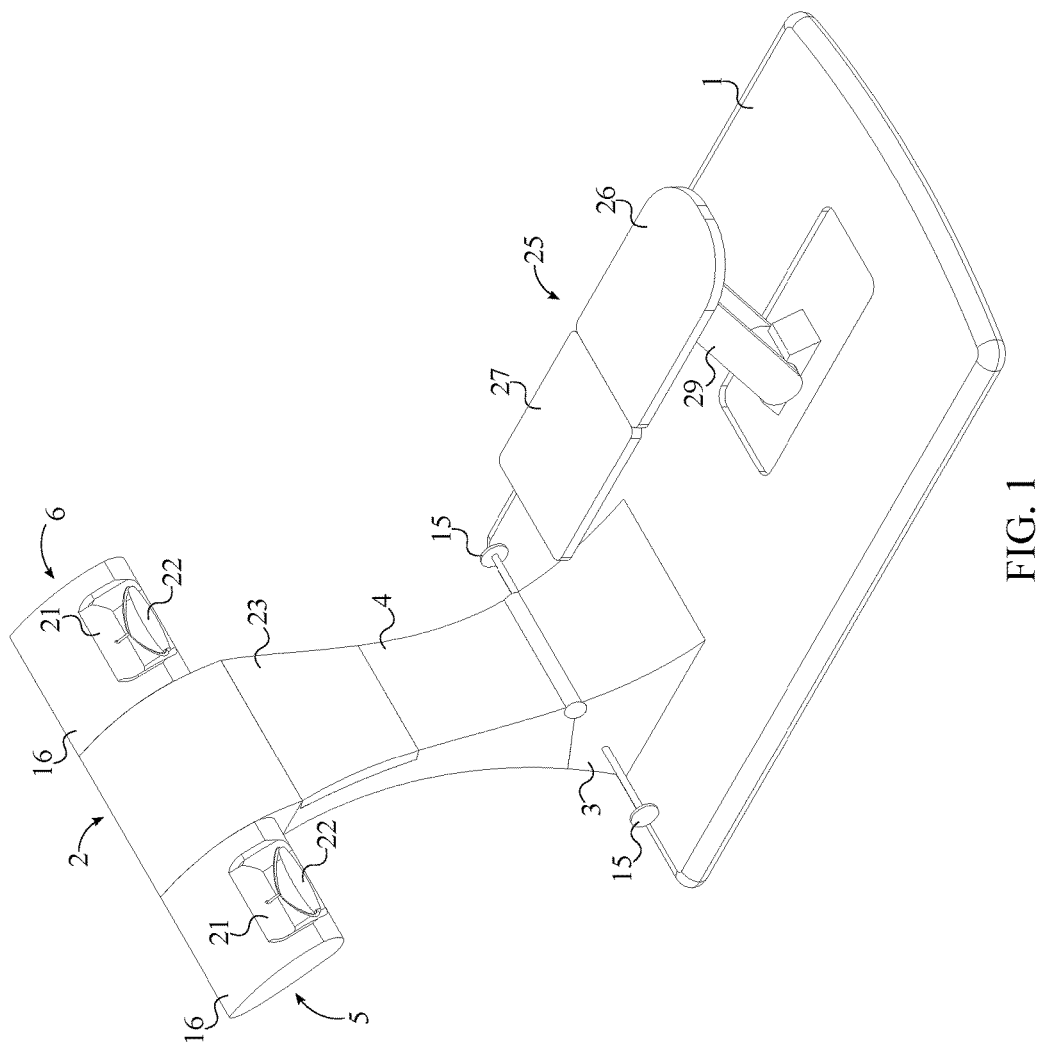
FIG. 1 is a perspective view of the present invention.
Figure 2:
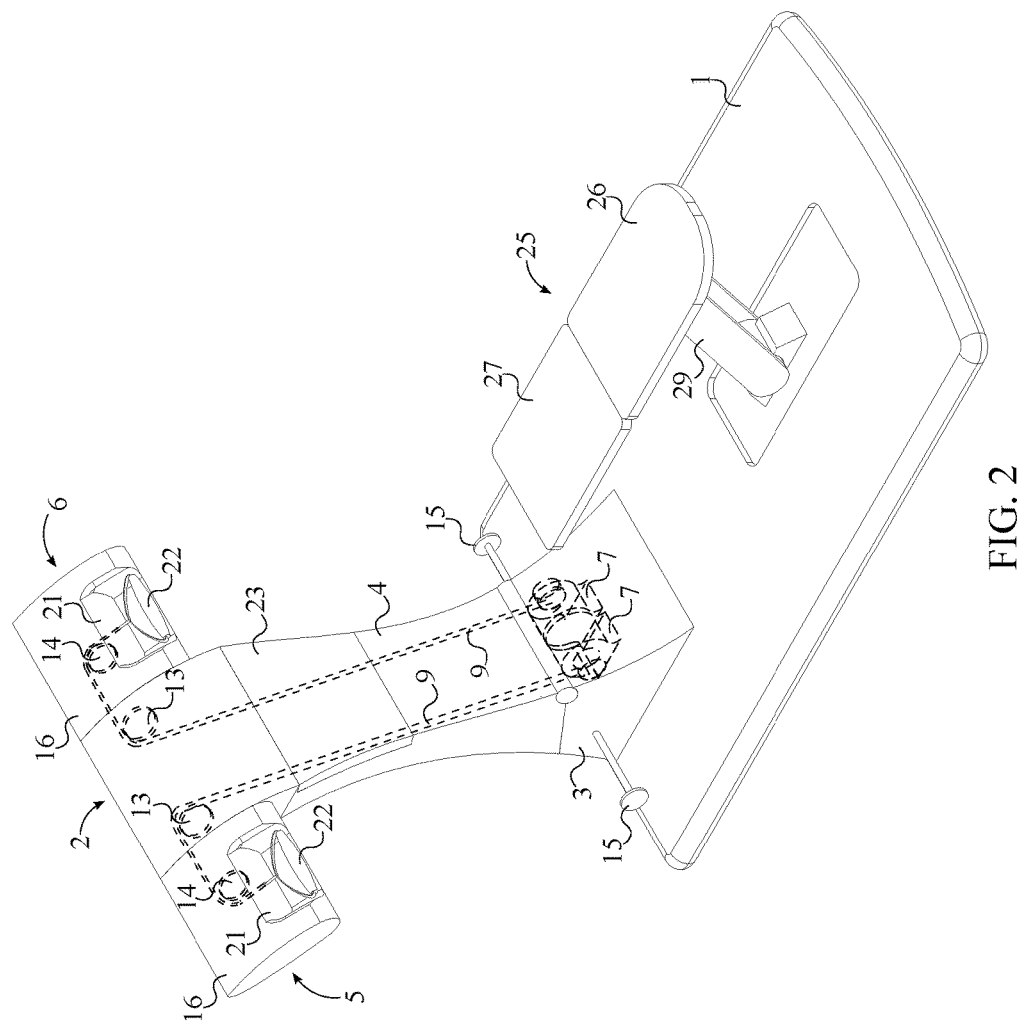
FIG. 2 is a semi-transparent perspective view of the present invention, fully illustrating an upper-left exercise module and an upper-right exercise module.
Figure 3:
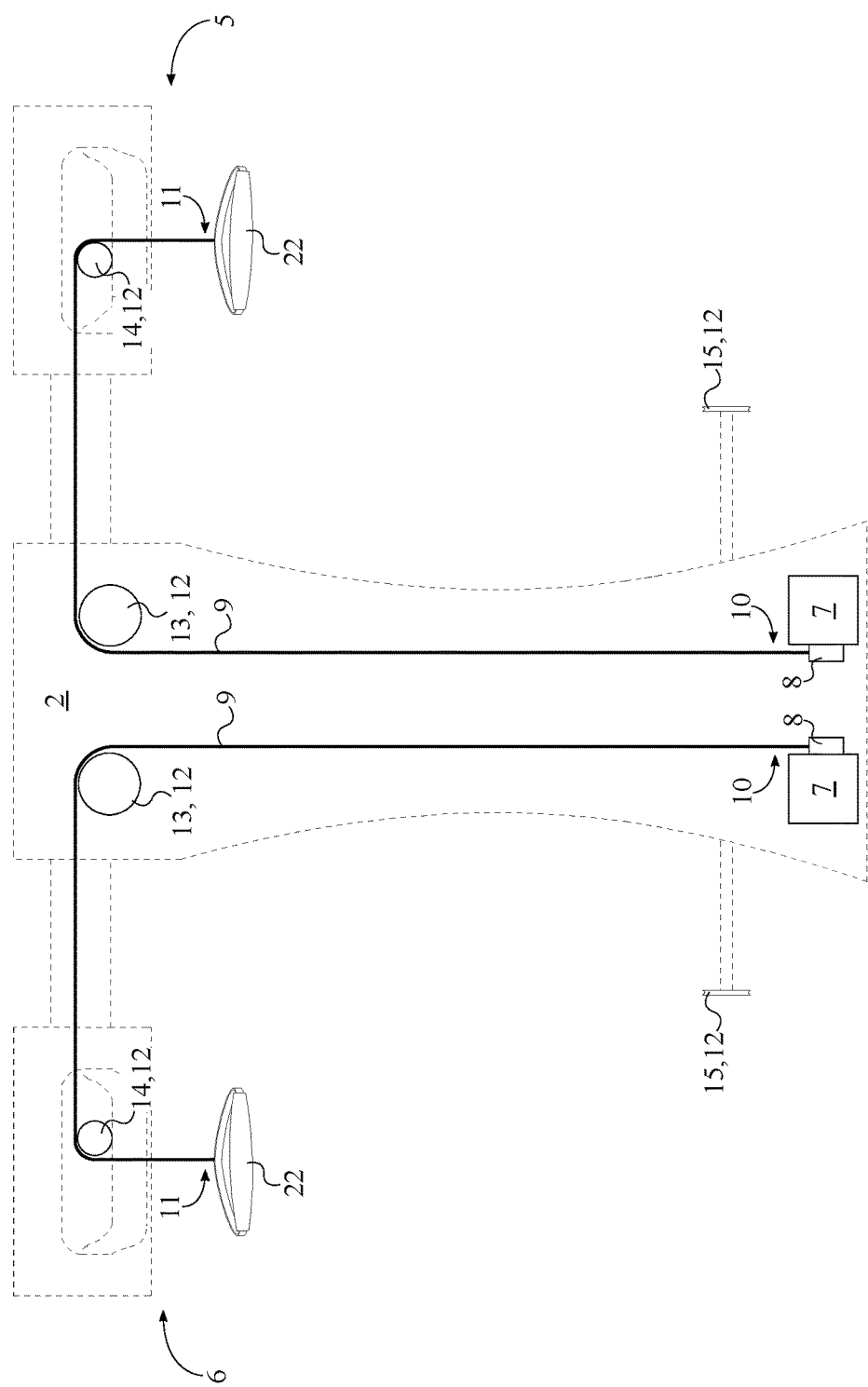
FIG. 3 is a schematic diagram of the present invention, depicting the upper-left exercise module and the upper-right exercise module.

Referring to FIG. 1 through FIG. 3, the present invention comprises a platform base 1, a housing tower 2, an upper-left exercise module 5, and an upper-right exercise module 6. The platform base 1 serves as a level structure which supports the housing tower 2, the upper-left exercise module 5, and the upper-right exercise module 6. Additionally, the platform base 1 provides the user with a level surface to stand on while utilizing the present invention. A multitude of rollers may be integrated into a bottom surface of the platform base 1 to allow the user to move the whole apparatus with ease. The rollers may be affixed to the platform base 1 or may be retractably connected to the platform base 1. The housing tower 2 is connected onto the platform base 1, preferably in a perpendicular orientation and towards a front end of the housing tower 2. The housing tower 2 houses, supports, and positions the respective constituents of the upper-left exercise module 5 and the upper-right exercise module 6. More specifically, the housing tower 2 positions the upper-left exercise module 5 and the upper-right exercise module 6 at an elevated position where the user can more easily engage the aforementioned components.

The upper-left exercise module 5 and the upper-right exercise module 6 produce the resistance force and provide a means for applying said force onto the extremities of the user. Referring to FIG. 2 and FIG. 3, the upper-left exercise module 5 and the upper-right exercise module 6 each comprise a primary torque motor 7, a primary cable 9, a pulley system 12, a structural arm 16, a primary handle stop 21, and a primary handle 22. The primary torque motor 7 generates the resistance force for the present invention. In particular, the primary torque motor 7 produces a torque force that can be held at a consistent level or changed instantly throughout an exercise. The present invention may also utilize a speed reducer and a servomotor in conjunction with the primary torque motor 7 in order to control the resistance force being generated by the primary torque motor 7. The aforementioned components may be used in order to change the resistance force linearly or within a preset curve, in both directions. The magnitude of the resistance force and the direction of the resistance force may change with slack-off of motion to zero, prior to reverse primary cable 9 motion. The primary torque motor 7 of the upper-left exercise module 5 and the primary torque motor 7 of the upper-right exercise module 6 are mounted within the housing tower 2, preferably adjacent to the platform base 1 as seen in FIG. 2. The primary handle 22 is the component through which the user interacts and engages the present invention. The primary handle 22 is preferably shaped to compliment the contours of the human hand and may contain cushioned pads for additional comfort. The primary handle 22 is mechanically coupled to the primary torque motor 7 by the primary cable 9. More specifically, a first end 10 of the primary cable 9 is fixed and coiled about an output 8 of the primary torque motor 7, while a second end 11 of the primary cable 9 is fixed to the primary handle 22. The primary cable 9 is tensionably engaged to the pulley system 12 in order to transfer the resistance force from the primary torque motor 7 to the primary handle 22, and therefore the user. In the event when the user drops the primary handle 22, the primary torque motor 7 decreases the force being applied onto the primary cable 9 to a minimal setting in order to slowly retract the primary handle 22. Additionally, the present invention eliminates any backlash or dead stretches during reel-out and cogging sensation while applying the resistance force to the primary handle 7.

Figure 4:
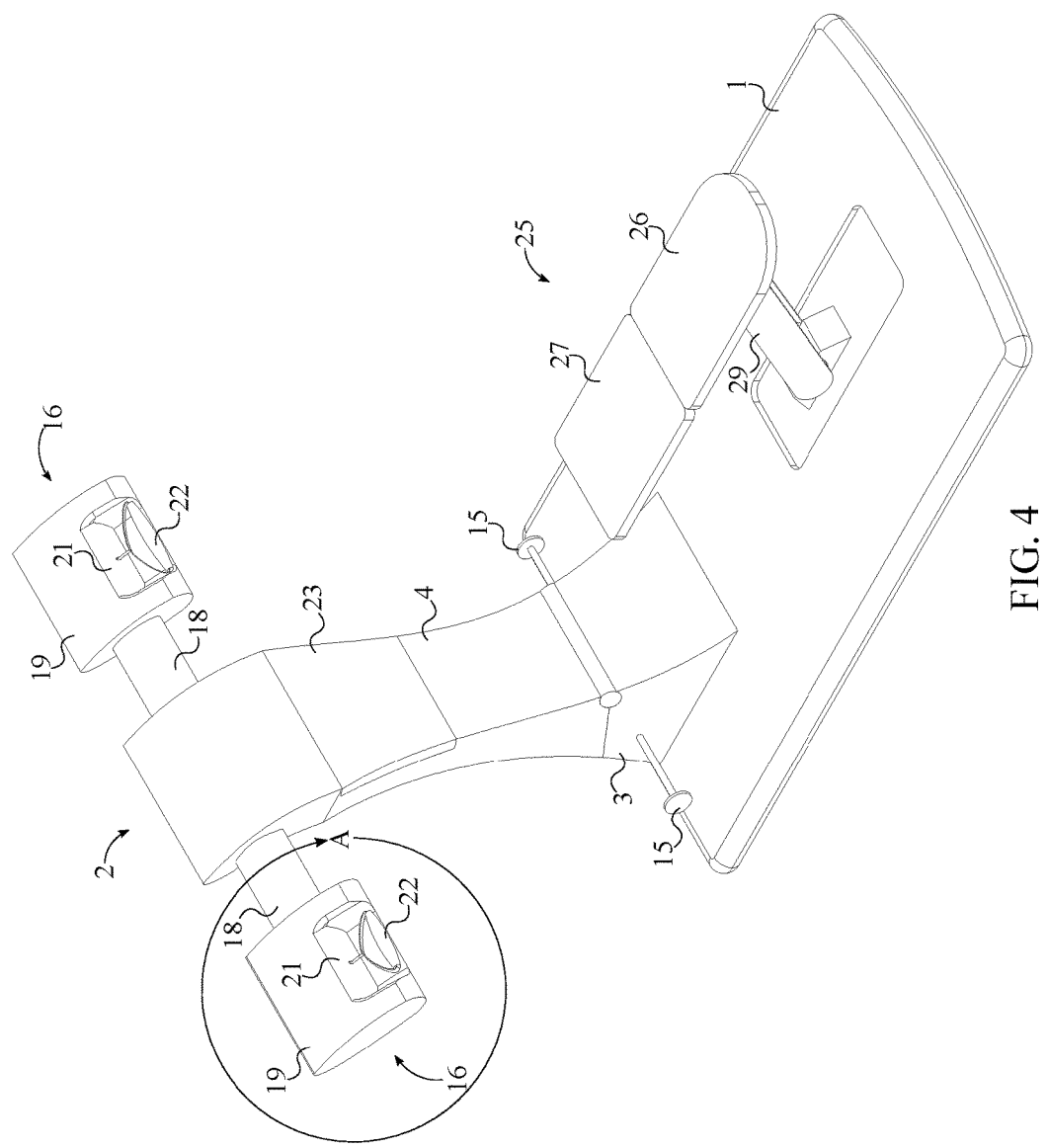
FIG. 4 is a perspective view of the present invention in an extended configuration.
Figure 5:
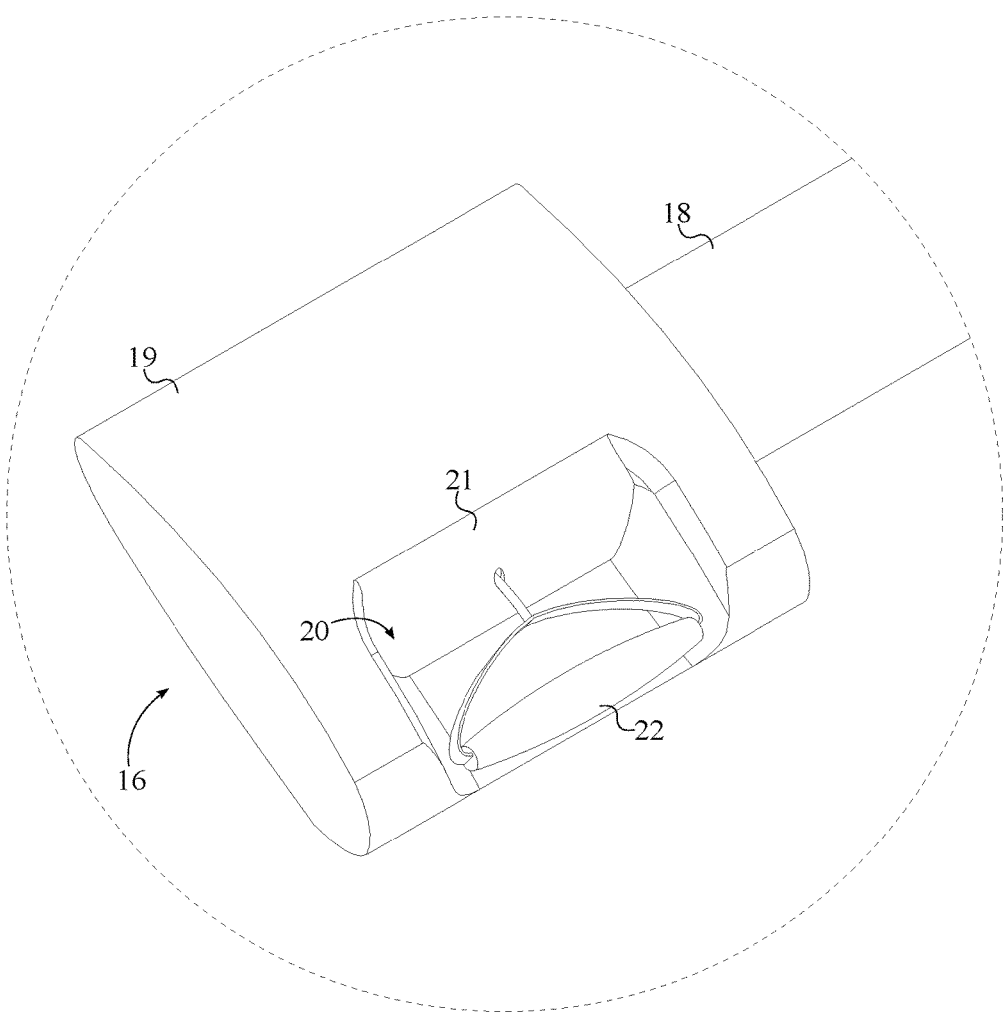
FIG. 5 is a detailed view taken about circle A in FIG. 4.

The structural arm 16 in conjunction with the primary handle stop 21 position and retain the primary handle 22 at an elevated state, along a side of the housing tower 2. The structural arm 16 is laterally connected to the housing tower 2, opposite the platform base 1. More specifically, the structural arm 16 of the upper-left exercise module 5 and the structural arm 16 of the upper-right exercise module 6 are positioned opposite of each other about the housing tower 2, resulting in a T-shaped structure. Referring to FIG. 5, the structural arm 16 comprises a telescoping shaft 18, a lateral housing structure 19, and a handle-receiving cavity 20. The telescoping shaft 18 is positioned adjacent to the housing tower 2 and allows for the structural arm 16 to laterally translate relative to the housing tower 2. Referring to FIG. 4, different positioning of the structural arm 16 change the angle at which the resistance force is applied to the user's hand, thus engaging different muscle groups. The lateral housing structure 19 houses and supports constituents of the pulley system 12 and receives the primary handle 22. The lateral housing structure 19 is adjacently connected to the telescoping shaft 18, opposite the housing tower 2.

The handle-receiving cavity 20 traverses into the lateral housing structure 19 and is sized to the dimensions of the primary handle 22 to facilitate a complimentary mounting point for the primary handle 22. The primary handle stop 21 is essentially a sidewall that is adjacently integrated to a distal end 17 of the structural arm 16 and is used to stop and prevent the primary handle 22 from travelling into the structural arm 16 as seen in FIG. 5. More specifically, the primary handle stop 21 is positioned within the handle-receiving cavity 20. When the present invention is not being used, the primary handle 22 rests within the handle-receiving cavity 20, pressing against the primary handle stop 21. The second end 11 of the primary cable 9 traverses through the primary handle stop 21 to connect the primary handle 22 to the primary torque motor 7.

The pulley system 12 supports the movement and change of direction of the primary cable 9 in order to connect the primary torque motor 7 to the primary handle 22 with as little friction as possible. The pulley system 12 is mounted within the housing tower 2 and the structural arm 16 as seen in FIG. 2. The pulley system 12 may include a number of pulleys distributed about the interior of the housing tower 2 in any fashion. In the preferred embodiment of the present invention, the pulley system 12 comprises a first pulley 13 and a second pulley 14. The first pulley 13 is internally mounted within an upper support structure 4 of the housing tower 2 in order to redirect the primary cable 9 into the structural arm 16. More specifically, the first pulley 13 of the upper-left exercise module 5 is positioned adjacent to the structural arm 16 of the upper-left exercise module 5; similarly, the first pulley 13 of the upper-right exercise module 6 is positioned adjacent to the structural arm 16 of the upper-right exercise module 6. The second pulley 14 is internally mounted within the structural arm 16, adjacent to the primary handle stop 21, in order to redirect the primary cable 990 degrees towards the primary handle stop 21. The handle-receiving cavity 20 is positioned adjacent to the second pulley 14 to ensure the primary handle 22 is directly in front of the second pulley 14. The first pulley 13 and the second pulley 14 are free to rotate about their respective main axes, thus facilitating smooth translation of the primary cable 9 within the housing tower 2 and the structural arm 16.

In the preferred embodiment of the present invention, the pulley system 12 further comprises a third pulley 15. The third pulley 15 is positioned external to the housing tower 2 and provides the user with an option to perform additional exercises. This is achieved by running/guiding the primary cable 9 through the third pulley 15. Referring to FIG. 1 and FIG. 2, the third pulley 15 of the upper-left exercise module 5 is positioned in between the structural arm 16 of the upper-left exercise module 5 and the platform base 1. Additionally, the third pulley 15 of the upper-left exercise module 5 is rotatably and laterally mounted to the housing tower 2. Similarly, the third pulley 15 of the upper-right exercise module 6 is positioned in between the structural arm 16 of the upper-right exercise module 6 and the platform base 1. Additionally, the third pulley 15 of the upper-right exercise module 6 is rotatably and laterally mounted to the housing tower 2. In one embodiment, the present invention also includes an ankle strap which wraps around the user's ankle and connects to the primary handle 22 or the primary cable 9. The ankle strap in conjunction with the third pulley 15 allows the user to engage muscle groups in the leg. This is achieved by running the primary cable 9 through the third pulley 15 and attaching the primary cable 9 to the user's leg through the use of the ankle strap.

Figure 9:
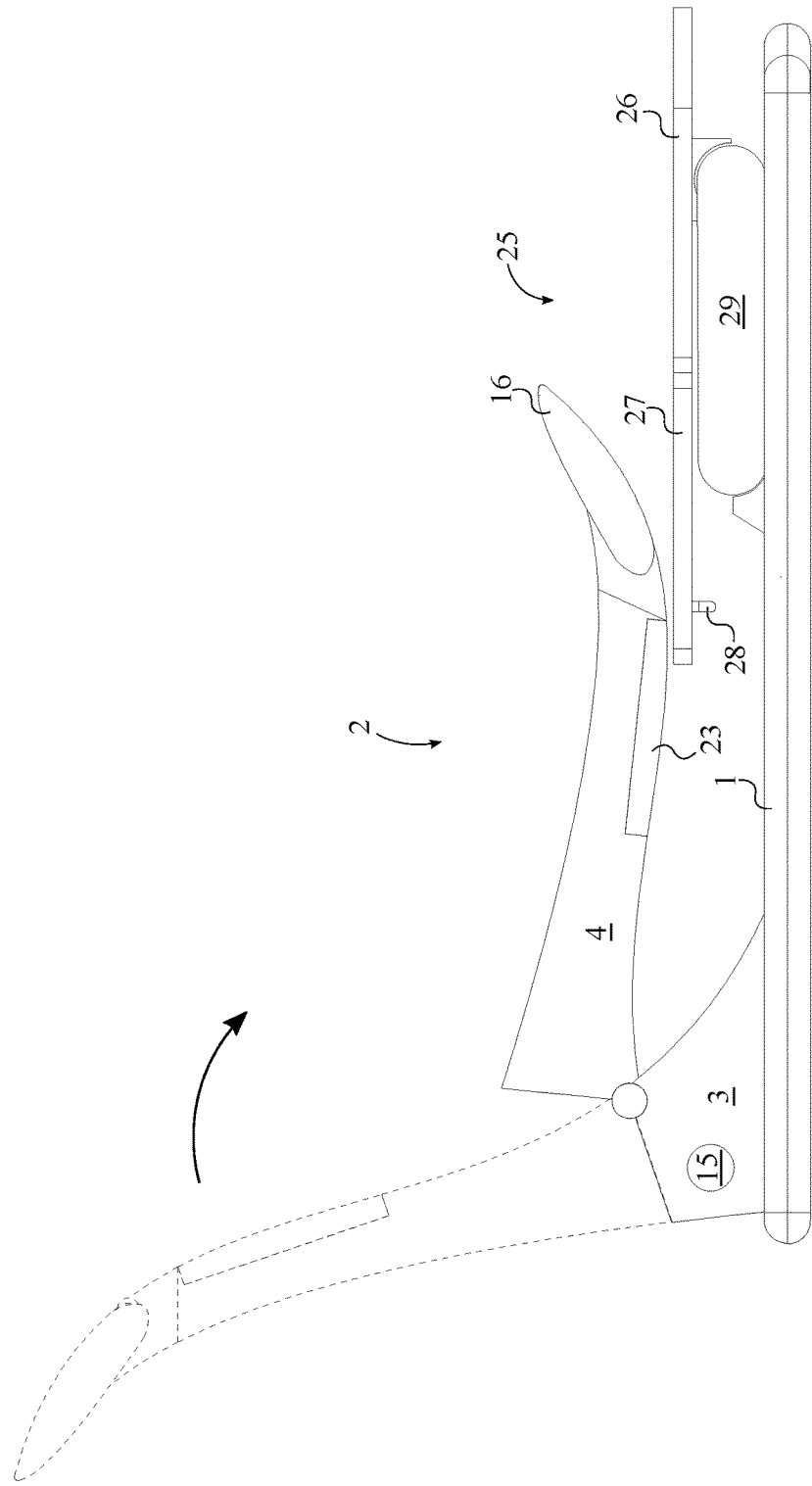
FIG. 9 is a side-view of the present invention, depicting a collapsed configuration.

In one embodiment, referring to FIG. 9, the present invention can be positioned into a collapsed configuration for storage purposes. This is achieved mainly through the housing tower 2. The housing tower 2 comprises a lower support structure 3 and the upper support structure 4. The lower support structure 3 is positioned adjacent to the platform base 1 and houses the primary torque motor 7 of the upper-left exercise module 5 and the primary torque motor 7 of the upper-right exercise module 6. The upper support structure 4 is positioned adjacent to the lower support structure 3, opposite the platform base 1. In order to allow the present invention to fold into the collapsed configuration, the upper support structure 4 is pivotably connected to the lower support structure 3. This allows the upper support structure 4 to rotate relative to the lower support structure 3 and the platform base 1 as seen in FIG. 9. The collapsed configuration is ideal for storing purposes. Additionally, the housing tower 2 facilitates heat dissipation through conduction, convection, louvered ventilation, or other means. Furthermore, various constituents of the present invention may be electromagnetically shielded to conform to traditional standards and regulations.

Figure 6:
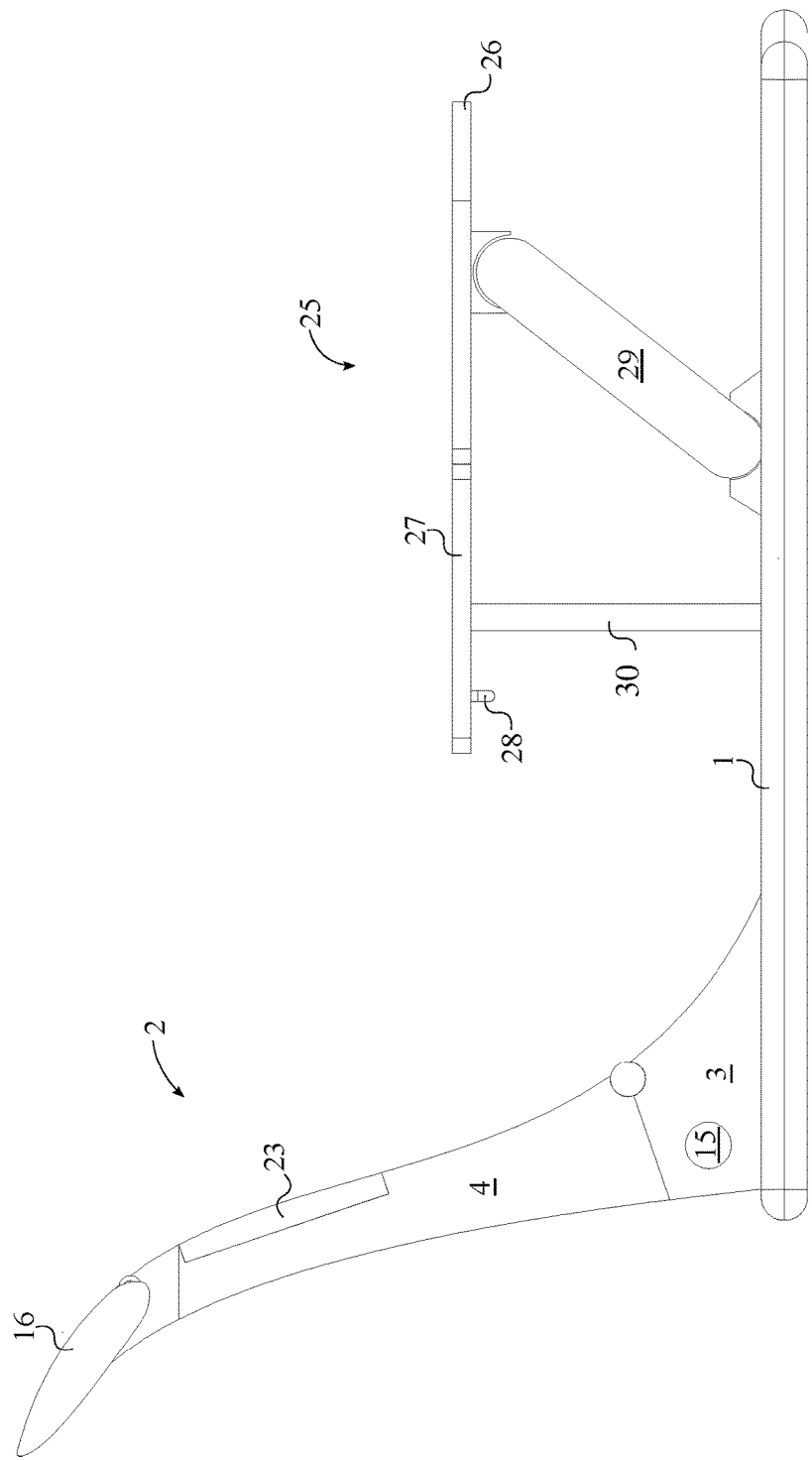
FIG. 6 is a side-view of the present invention, depicting a second support leg.
Figure 7:
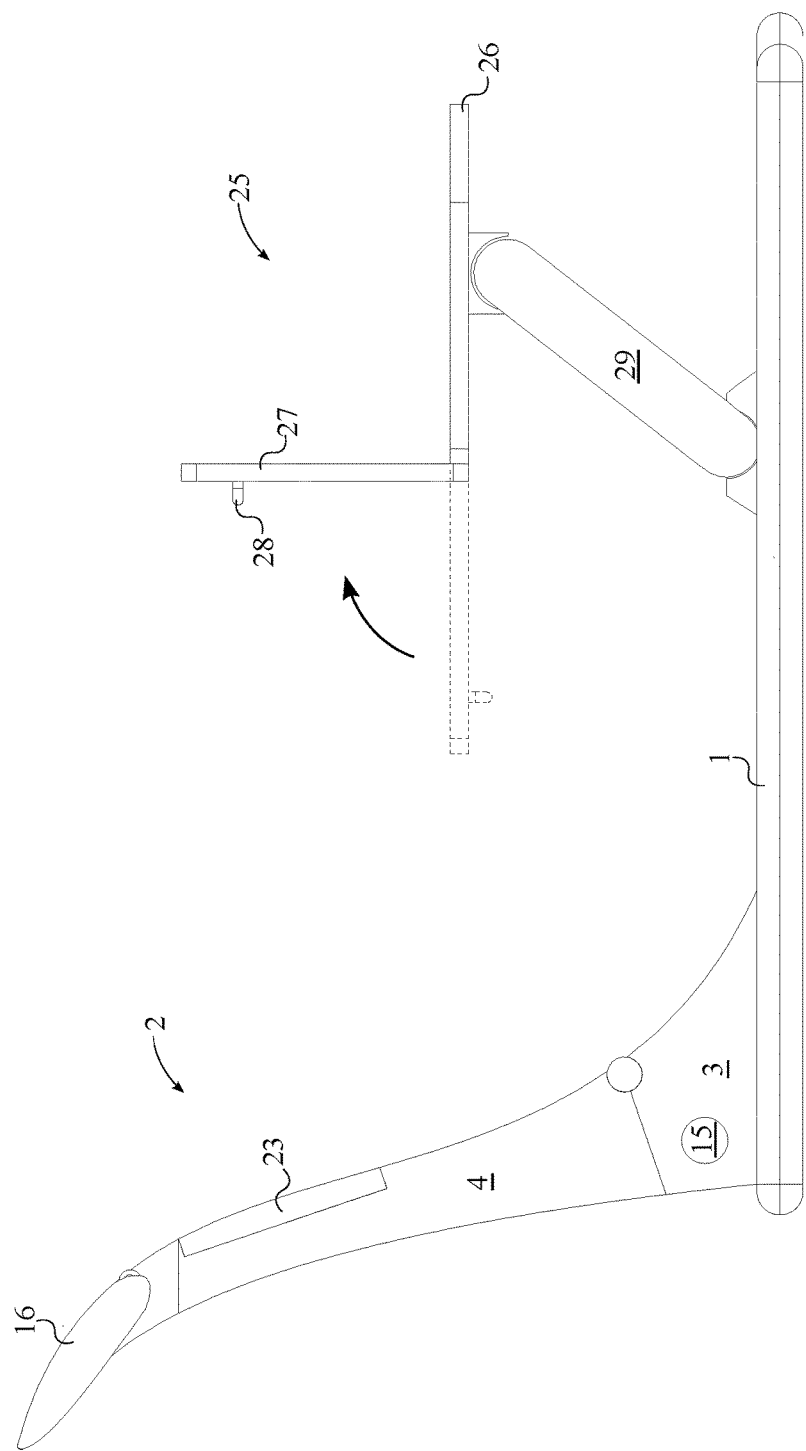
FIG. 7 is a side-view of the present invention, depicting a backrest of an adjustable seat being raised for lateral support.

In one embodiment, the present invention further comprises an adjustable seat 25, a first support leg 29, a second support leg 30, and a seat handle 28. The adjustable seat 25 allows the user to perform various exercises in a seated position, ideal for isolating and engaging specific muscle groups. The adjustable seat 25 is preferably cushioned as to provide a comfortable seat for the user. Referring to FIG. 1 and FIG. 6, the adjustable seat 25 is removably connected to the platform base 1 by the first support leg 29. In particular, the first support leg 29 is removably and pivotably attached to the platform base 1, allowing for height adjustment of the adjustable seat 25. The adjustable seat 25 is pivotably attached to the first support leg 29, opposite the platform base 1, which in turn allows the adjustable seat 25 to rotate relative to the first support leg 29. In one embodiment of the present invention, the adjustable seat 25 is rotatably attached to the first support leg 29, allowing the adjustable seat 25 to rotate parallel to the platform base 1 to suit the user needs.

Figure 8:
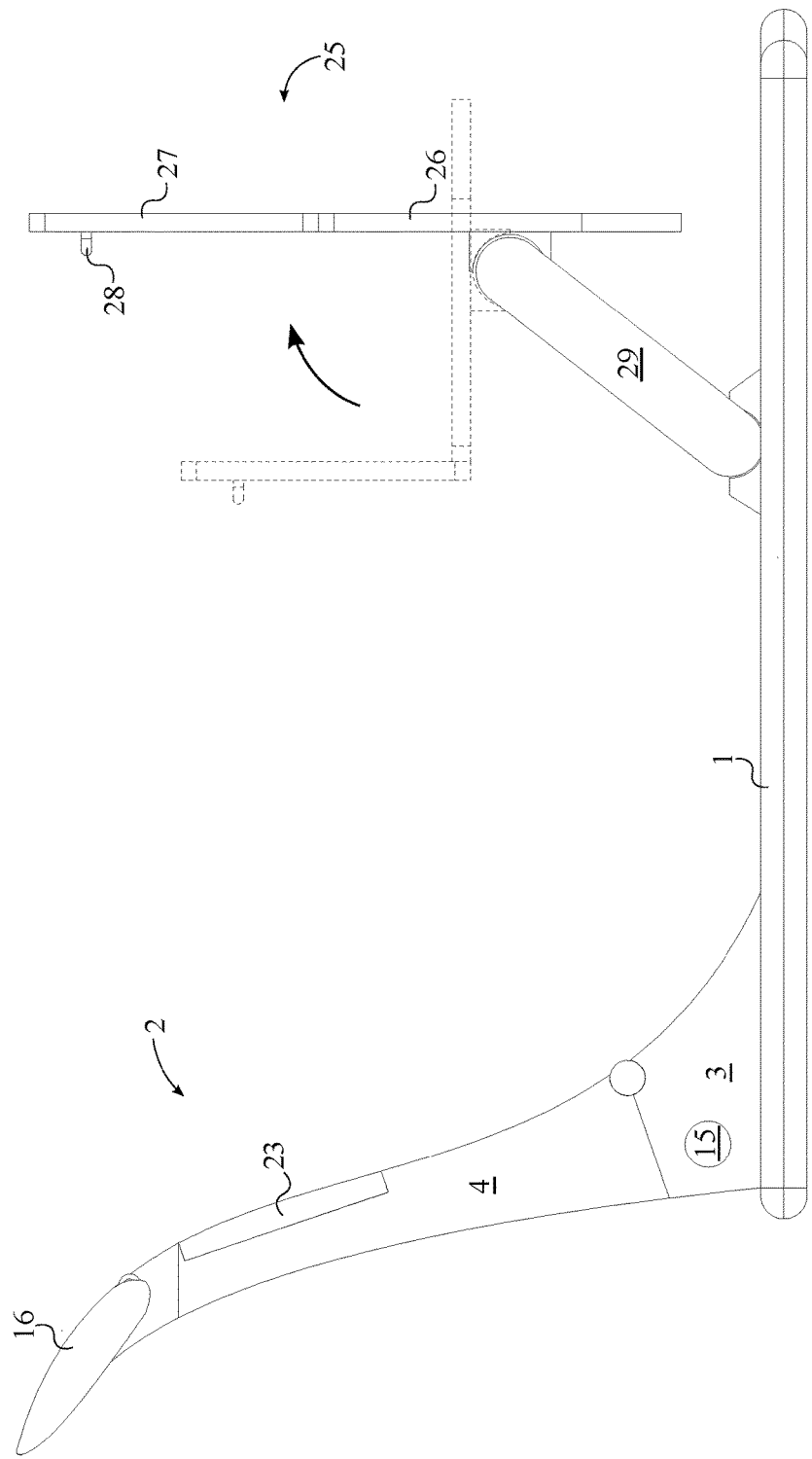
FIG. 8 is a side-view of the present invention, depicting the adjustable seat being raised into a vertical orientation.

The adjustable seat 25 further comprises a horizontal seat 26 and a backrest 27. The horizontal seat 26 acts as the flat surface on which the user may sit on while the backrest 27 acts as a back or chest support. The first support leg 29 is pivotably attached to the horizontal seat 26. The backrest 27 is adjacently and pivotably connected to the horizontal seat 26 in between the horizontal seat 26 and the housing tower 2. The junctions between the platform base 1, the first support leg 29, the horizontal seat 26, and the backrest 27 are each safely lockable to allow the user to lock the aforementioned components into various heights, orientations, and configurations. FIG. 6, FIG. 7, FIG. 8, and FIG. 9 illustrate some of the configurations which the adjustable seat 25 and the adjoining components may be positioned into. The seat handle 28 is positioned in between the platform base 1 and the adjustable seat 25, adjacently connected to the adjustable seat 25. The seat handle 28 is designed to stabilize the user when the adjustable seat 25 is positioned into a vertical orientation as seen in FIG. 8, during standing exercises.

Referring to FIG. 6, in cases where the adjustable seat 25 requires additional vertical support, the user may use a second support leg 30. A first end of the second support leg 30 is adjacently and perpendicularly connected to the platform base 1, directly underneath the adjustable seat 25. The adjustable seat 25 is removably attached to a second end of the second support leg 30, opposite the base. This configuration allows the adjustable seat 25 of the present invention to bear significantly more weight than when only the first support leg 29 is utilized. For example, the second support leg 30 is useful if the user introduces free weights into his or her exercise routines in conjunction with the present invention, thus requiring additional vertical support. In alternative embodiments of the present invention, alternative mechanism may be attached to the platform base 1 instead of the adjustable seat. Such mechanisms include, but are not limited to, exercise bikes, rowing machines, and other similar devices. The aforementioned mechanism would also be able to connect to the present invention through a wireless or wired connected in order display exercise data to the user and interact further with the control console.

Figure 10:
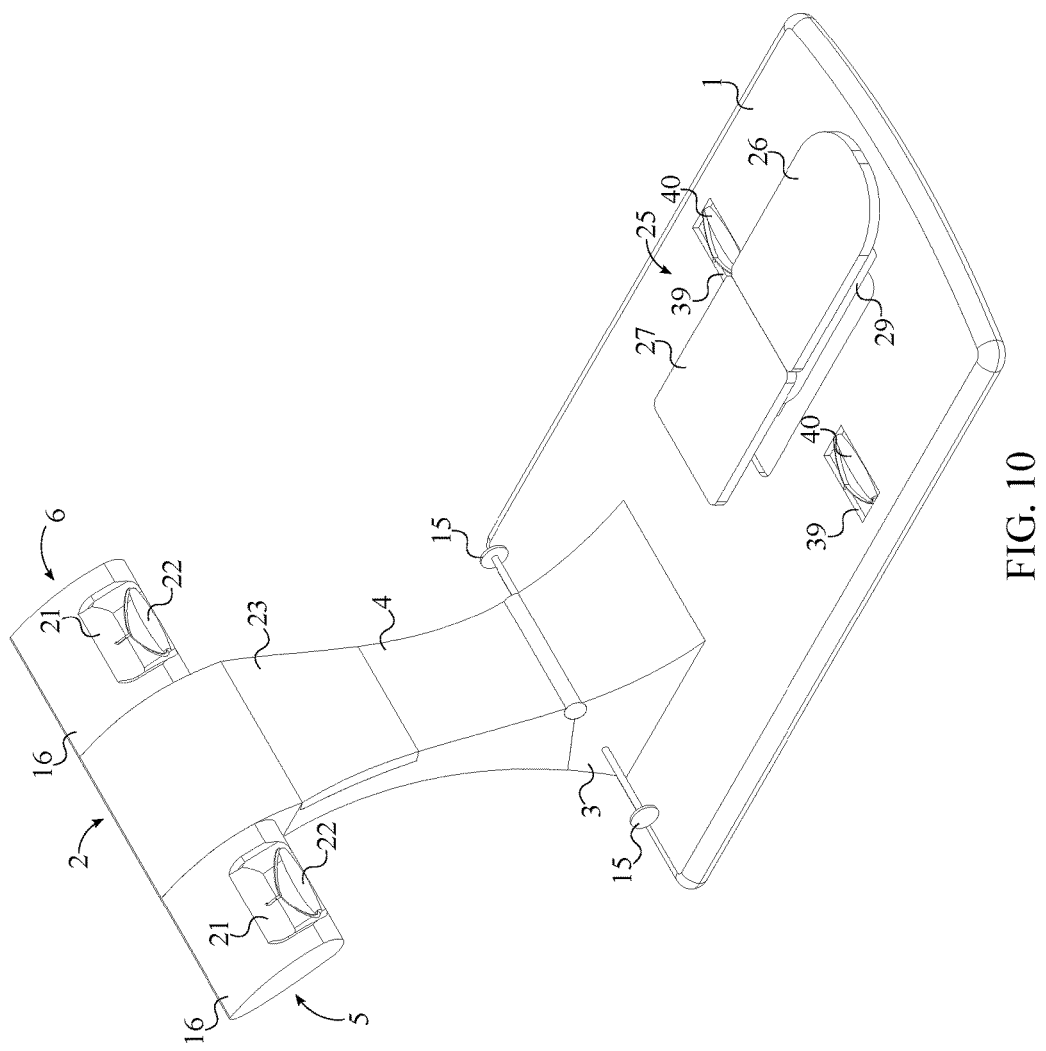
FIG. 10 is a perspective view of an alternative embodiment of the present invention.
Figure 11:
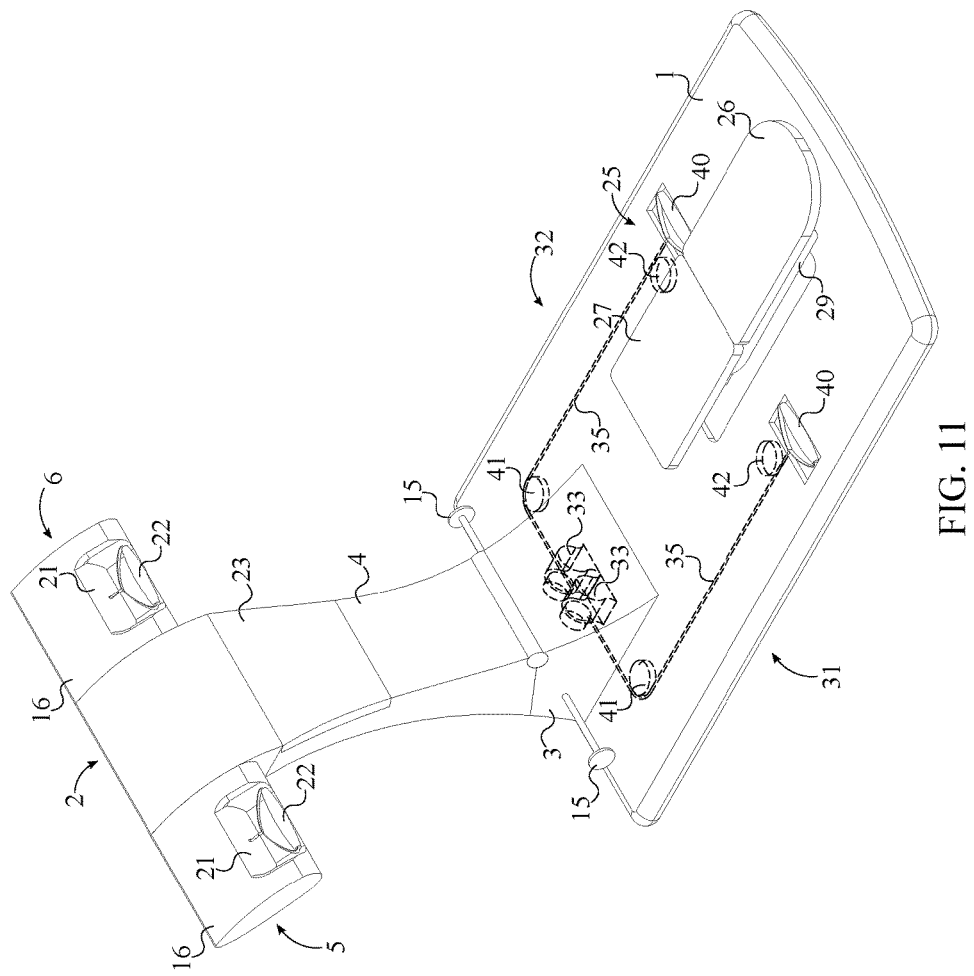
FIG. 11 is a semi-transparent perspective view of the alternative embodiment of the present invention, fully illustrating a lower-left exercise module and a lower-right exercise module.
Figure 12:
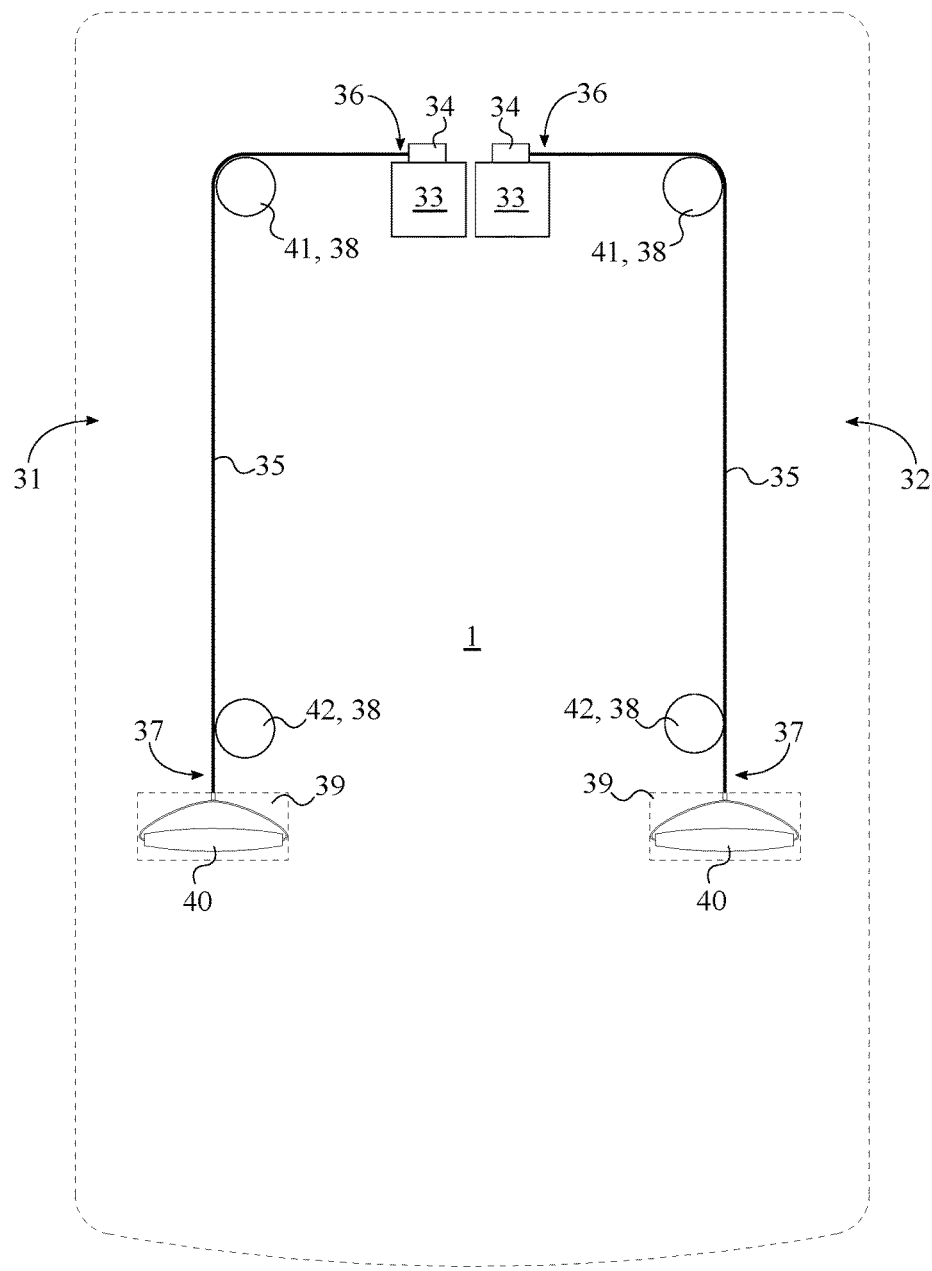
FIG. 12 is a schematic diagram of the present invention, depicting the lower-left exercise module and the lower-right exercise module.

Referring to FIG. 10 and FIG. 11, the present invention further comprises a lower-left exercise module 31 and a lower-right exercise module 32. The lower-left exercise module 31 and the lower-right exercise module 32 produce an additional resistance force and provide a means for applying said force onto the extremities of the user, preferably the lower extremities of the user. Referring to FIG. 11 and FIG. 12, the lower-left exercise module 31 and the lower-right exercise module 32 each comprise a secondary torque motor 33, a secondary cable 35, a lateral pulley system 38, a secondary handle stop 39, and a secondary handle 40. The secondary torque motor 33 generates the resistance force for the secondary handle 40 Similar to the primary torque motor 7, the secondary torque motor 33 produces a torque force that can be held at a consistent level or changed instantly throughout an exercise. The secondary torque motor 33 of the lower-left exercise module 31 and the secondary torque motor 33 of the lower-right exercise module 32 are mounted within the housing tower 2, preferably adjacent to the platform base 1 as seen in FIG. 11. Alternative mounting positions may also be utilized in alternative embodiments of the present invention. In one embodiment of the present invention, the primary torque motor 7 of the upper-left exercise module 5 is coupled to both to the primary handle 22 of the upper-left exercise module 5 and the secondary handle 39 of the lower-left exercise module 31; similarly, the primary torque motor 7 of the upper-right exercise module 6 is coupled to both to the primary handle 22 of the upper-right exercise module 6 and the secondary handle 39 of the lower-right exercise module 32.

The secondary handle 40 is the component through which the user interacts and engages the present invention, the lower-left exercise module 31 and the lower-right exercise module 32 in particular. The secondary handle 40 is preferably shaped to compliment the contours of the human hand and may contain cushioned ridges. The secondary handle 40 is mechanically coupled to the secondary torque motor 33 by the secondary cable 35. A first end 36 of the secondary cable 35 is fixed and coiled about an output 34 of the secondary torque motor 33, while a second end 37 of the secondary cable 35 is fixed to the secondary handle 40. The body of the secondary cable 35 is positioned within the platform base 1 and is guided from the secondary torque motor 33 to the secondary handle stop 39 by the lateral pulley system 38. The second end 37 of the secondary cable 35 traverses through the secondary handle stop 39 in order to connect with the secondary handle 40. To efficiently transfer the additional resistance force, the secondary cable 35 is tensionably engaged to the lateral pulley system 38 as seen in FIG. 12. The secondary handle stop 39 is essentially a sidewall that is adjacently integrated into the platform base 1 which is used to stop and prevent the secondary handle 40 from travelling into the platform base 1 as seen in FIG. 10. More specifically, the secondary handle stop 39 of the lower-left exercise module 31 and the secondary handle stop 39 of the lower-right exercise module 32 are positioned opposite of each other about the housing tower 2 as seen in FIG. 12. This configuration positions the secondary handle stop 39 of the lower-left exercise module 31 directly to the side of the user's left foot and the secondary handle stop 39 of the lower-right exercise module 32 directly to the side of the user's right foot. When the present invention is not being used, the secondary handle 40 rests against the secondary handle stop 39.

The lateral pulley system 38 supports the movement and change of direction of the secondary cable 35 in order to connect the secondary torque motor 33 to the secondary handle 40 with as little friction as possible. The lateral pulley system 38 is mounted within the platform base 1 as seen in FIG. 11. The lateral pulley system 38 may include a number of pulleys distributed about the interior of the platform base 1 in any fashion. It is preferred that the lateral pulley system 38 comprises a proximal pulley 41 and a distal pulley 42. The proximal pulley 41 is internally mounted within the platform base 1, adjacent to the housing tower 2 in order to redirect the secondary cable 35 towards the secondary handle stop 39. More specifically, the proximal pulley 41 of the lower-left exercise module 31 is positioned opposite the proximal pulley 41 of the lower-right exercise module 32 and across the housing tower 2. The distal pulley 42 is internally mounted within the platform base 1, adjacently to the secondary handle stop 39, in order to facilitate the translation of the secondary cable 35 through the secondary handle stop 39. The proximal pulley 41 and the distal pulley 42 are free to rotate about their respective main axes, thus facilitating smooth translation of the secondary cable 35.

Figure 13:
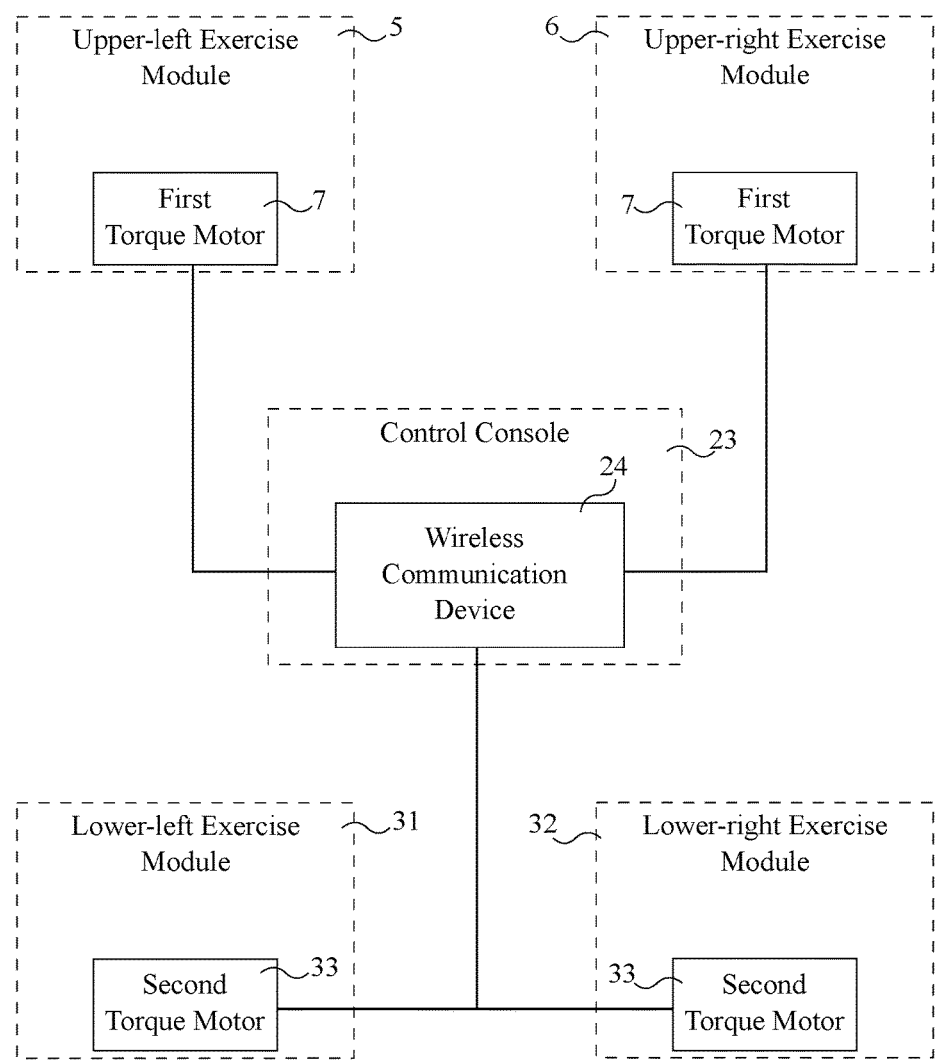
FIG. 13 is an electronic diagram of the present invention.

Referring to FIG. 13, the present invention further comprises a control console 23 as a user interface for the exercise machine. The control console 23 is integrated into the upper support structure 4 to provide the user with easy access to the control console 23. The control console 23 is electronically connected to the primary torque motor 7 of the upper-left exercise module 5 and the primary torque motor 7 of the upper-right exercise module 6. In the alternative embodiment, the control console 23 is electronically connected to the secondary torque motor 33 of the lower-left exercise module 31 and the secondary torque motor 33 of the lower-right exercise motor. Through the control console 23, the user is able to control various aspects of the present invention such as resistance force settings. The control console 23 in conjunction with the primary torque motor 7 provides the user with a constant resistance setting, a varying resistance setting, and other varying profile of resistances. A profile of resistance dictates the resistance force being generated by the primary torque motor 7 based on the positioning of the primary handle 22. One example includes the resistance force gradually increasing as the primary handle 22 is pulled further away from the structural arm 16; and gradually decreasing as the primary handle 22 is released and retracted closer to the structural arm 16. The present invention provides the user with a variety of profiles and allows the user to generate/create his or her own preferred profile. The control console 23 may include a wireless communication device 24, a universal serial bus (USB), a touchscreen, and a set of controls buttons. The wireless communication device 24 allows various external computing devices to connect, control, and interact with the present invention. External computing devices include, but are not limited to, smartphones, tablets, and laptops. The housing tower 2 may also include a device docking station for holding external computing devices. The present invention uses a variety of sensors to measure speed and distance moved of the primary cable 9 and/or the secondary cable 35. This information is used to determine resistance force, number of repetitions, angle of repetitions, speed of repetitions, and other similar descriptive information. The user may view any of this information on his or her external computing device and/or through the control console 23 in real time. In one embodiment, the present invention provides forced feedback in concert with an external application that is connected to the present invention.

The present invention creates a user account for the user which includes the user's name, gender, age, weight, and general health to name a few non-limiting examples. This information in conjunction with performance information is used to generate an overall strength of the user, also called SQ. The SQ is a measure of individual strength, just like IQ is a measure of intelligence. The present invention prompts the user to perform six exercises in order to gather descriptive information about the user. Each of the exercises is designed to target and measure a specific muscle group (arms, legs, back, chest, abs and shoulders). At the end of the test the present invention takes the descriptive information and generates an SQ number, a number between 0-300.

The present invention comes with three apps, weight loss, muscle toning, and tennis conditioning. The weight loss application includes 10 exercises that are performed in a "super set" way, i.e. 10 exercises continuously without a break at 40 percent of the user's max SQ for each muscle group. At the end of the session, the present invention will display calories burned each session. The resistance force will increase weekly based on the user's fitness level (beginner, intermediate, advanced). For the muscle toning application, the user will be performing three sets of ten exercises for 10-12 reps at 80 percent of the user's SQ max. Once the user is able to do 13 reps easily or after one week the system will automatically increase the resistance force for each exercise based on the user's fitness level. The tennis muscle toning app includes 10 exercises pertinent to muscles used for playing tennis. The user will perform the exercises in the same format as the muscle toning application.

Although the invention has been explained in relation to its preferred embodiment, it is to be understood that many other possible modifications and variations can be made without departing from the spirit and scope of the invention as hereinafter claimed.

What is claimed is:

1. A multi-position exercise machine with dynamic resistance comprises:
   a platform base;
   a housing tower;
   an upper-left exercise module;
   an upper-right exercise module;
   a control console;
   the upper-left exercise module and the upper-right exercise module each comprises a primary torque motor, a primary cable, a pulley system, a structural arm, a primary handle stop, and a primary handle;
   the housing tower being connected onto the platform base;
   the primary torque motor of the upper-left exercise module and the primary torque motor of the upper-right exercise module being mounted within the housing tower;
   the structural arm being laterally connected to the housing tower, opposite the platform base;
   the structural arm of the upper-left exercise module and the structural arm of the upper-right exercise module being positioned opposite of each other about the housing tower;
   the pulley system being mounted within the housing tower and the structural arm;

the primary handle stop being adjacently integrated to a distal end of the structural arm;

the primary cable tensionably engaging the pulley system;

a first end of the primary cable being fixed and coiled about an output of the primary torque motor;

a second end of the primary cable traversing through the primary handle stop; and the second end of the primary cable being fixed to the primary handle;

the control console being integrated into an upper support structure of the housing tower;

the control console being electronically connected to the primary torque motor of the upper-left exercise module and the primary torque motor of the upper-right exercise module;

an adjustable seat;

a first support leg;

the first support leg being removably and pivotably attached to the platform base;

the adjustable seat being pivotably attached to the first support leg, opposite the platform base;

the adjustable seat comprises a horizontal seat and a backrest;

the first support leg being pivotably attached to the horizontal seat;

the backrest being positioned in between the horizontal seat and the housing tower; and the backrest being adjacently and pivotably connected to the horizontal seat.

2. The multi-position exercise machine with dynamic resistance as claimed in claim 1 comprises:

the housing tower comprises a lower support structure and an upper support structure;

the lower support structure being positioned adjacent to the platform base;

the upper support structure being positioned adjacent to the lower support structure, opposite the platform base; and the upper support structure being pivotably connected to the lower support structure.

3. The multi-position exercise machine with dynamic resistance as claimed in claim 1, wherein the control console includes a wireless communication device.

4. The multi-position exercise machine with dynamic resistance as claimed in claim 1 comprises:

the pulley system comprises a first pulley and a second pulley;

the first pulley being internally mounted within an upper support structure of the housing tower;

the second pulley being internally mounted within the structural arm, adjacent to the primary handle stop;

the first pulley of the upper-left exercise module being positioned adjacent to the structural arm of the upper-left exercise module; and the first pulley of the upper-right exercise module being positioned adjacent to the structural arm of the upper-right exercise module.

5. The multi-position exercise machine with dynamic resistance as claimed in claim 1 comprises:

the structural arm comprises a telescoping shaft, a lateral housing structure, and a handle-receiving cavity;

the telescoping shaft being positioned adjacent to the housing tower;

the lateral housing structure being adjacently connected to the telescoping shaft, opposite the housing tower;

the handle-receiving cavity traversing into the lateral housing structure, adjacent to a second pulley from the pulley system; and the primary handle stop being positioned within the handle-receiving cavity.

6. The multi-position exercise machine with dynamic resistance as claimed in claim 1 comprises:

the pulley system further comprises a third pulley;

the third pulley of the upper-left exercise module being positioned in between the structural arm of the upper-left exercise module and the platform base;

the third pulley of the upper-left exercise module being rotatably and laterally mounted to the housing tower;

the third pulley of the upper-right exercise module being positioned in between the structural arm of the upper-right exercise module and the platform base; and the third pulley of the upper-right exercise module being rotatably and laterally mounted to the housing tower.

7. The multi-position exercise machine with dynamic resistance as claimed in claim 1 comprises:

a lower-left exercise module;

a lower-right exercise module;

the lower-left exercise module and the lower-right exercise module each comprises a secondary torque motor, a secondary cable, a lateral pulley system, a secondary handle stop, and a secondary handle;

the secondary torque motor of the lower-left exercise module and the secondary torque motor of the lower-right exercise module being mounted within the housing tower;

the secondary handle stop being adjacently integrated into the platform base;

the secondary handle stop of the lower-left exercise module and the secondary handle stop of the lower-right exercise module being positioned opposite of each other about the housing tower;

the lateral pulley system being mounted within the platform base;

the secondary cable tensionably engaging the lateral pulley system;

a first end of the secondary cable being fixed and coiled about an output of the secondary torque motor;

a second end of the secondary cable traversing through the secondary handle stop;

the second end of the secondary cable being fixed to the secondary handle; and the control console being electronically connected to the secondary torque motor of the lower-left exercise module and the secondary torque motor of the lower-right exercise module.

8. The multi-position exercise machine with dynamic resistance as claimed in claim 7 comprises:

the lateral pulley system comprises a proximal pulley and a distal pulley;

the proximal pulley being internally mounted within the platform base, adjacent to the housing tower;

the distal pulley being internally mounted within the platform base, adjacent to the secondary handle stop; and the proximal pulley of the lower-left exercise module being positioned opposite the proximal pulley of the lower-right exercise module across the housing tower.

9. The multi-position exercise machine with dynamic resistance as claimed in claim 1 comprises:

a seat handle;

the seat handle being positioned in between the platform base and the adjustable seat; and the seat handle being adjacently connected to the adjustable seat.

10. The multi-position exercise machine with dynamic resistance as claimed in claim 1 comprises:
- a second support leg;
- the second support leg being adjacently and perpendicularly connected to the platform base; and
- the adjustable seat being removably attached to the second support leg, opposite the platform base.

* * * * *